United States Patent [19]
Grunberg et al.

[11] 3,952,091
[45] Apr. 20, 1976

[54] SIMULTANEOUS MULTIPLE RADIOIMMUNOASSAY

[75] Inventors: Emanuel Grunberg, North Caldwell; Magdalena Usategui Gomez, Wayne, both of N.J.

[73] Assignee: Hoffmann-La Roche Inc., Nutley, N.J.

[22] Filed: Oct. 23, 1974

[21] Appl. No.: 517,268

[52] U.S. Cl. ............................. 424/1.5; 23/230 B; 23/230.3; 260/112 B; 424/12; 252/408
[51] Int. Cl.$^2$ ........................................ G01N 33/16
[58] Field of Search ............ 23/230 B, 230.3, 230.6; 424/1.5, 12; 260/112 B; 252/408

[56] References Cited
UNITED STATES PATENTS

| | | | |
|---|---|---|---|
| 3,704,282 | 11/1972 | Spector | 424/12 X |
| 3,709,868 | 1/1973 | Spector | 424/12 X |
| 3,766,162 | 10/1973 | Spector | 23/230 B X |
| 3,775,536 | 11/1973 | Spector | 23/230 B X |
| 3,799,741 | 3/1974 | Williams | 23/230 B |
| 3,826,619 | 7/1974 | Bratu, Jr. | 23/253 R |
| 3,843,696 | 10/1974 | Wagner | 424/12 X |
| 3,853,987 | 12/1974 | Dreyer | 23/230 B |
| 3,867,366 | 2/1975 | Rubenstein | 23/230 B X |
| 3,878,187 | 4/1975 | Schneider | 424/12 X |

*Primary Examiner*—Morris O. Wolk
*Assistant Examiner*—Sidney Marantz
*Attorney, Agent, or Firm*—Samuel L. Welt; George M. Gould

[57] ABSTRACT

Compositions useful for conducting a plurality of different radioimmuno-assays simultaneously and methods for preparing same. The compositions radioimmunoassaya a plurality of labeled antigens and their respective antibodies present in selected concentrations so that the response curves observed for each antigen are essentially superimposable on the response curve of all other antigens present in the composition. Particularly preferred compositions include a mixture of radiolabeled morphine, a radiolabeled 5- or 5,5-substituted barbituric acid, i.e., secobarbital and their respective antibodies useful for performing a bivalent radioimmunoassay and a mixture of radiolabeled morphine, radiolabeled amphetamine, a radiolabeled 5- or 5,5-substituted barbituric acid and their respective antibodies useful for performing a trivalent radioimmunoassay.

16 Claims, No Drawings

SIMULTANEOUS MULTIPLE RADIOIMMUNOASSAY

Background of the Invention

A large number of radioimmunoassays have been developed and commercially implemented in the last several years. The popularity of this analytical technique has been due in large measure to the fact that it is rapid, highly sensitive and amenable to automated procedures.

Many of the new radioimmunoassays have been directed to situations involving routine screening of biological fluids for the presence of a number of indicated substances where the majority of samples screened produce a negative indication, i.e., the substances being screened for are absent. However, in such cases, a number of samples from each subject are required and such samples must be repetitiously put through each test sequence. This obviously involves substantial duplication of technician time and effort as well as inefficient utilization of the instruments employed in carrying out the radioimmunoassay.

Procedures for preparing antigens and antibodies and for employing them in individual radioimmunoassays are well known in the art. For example, U.S. Pat. Nos. 3,709,868, 3,775,536 and 3,822,245 describe such methods with regard to a radioimmunoassay for opium alkaloids. U.S. Pat. No. 3,766,162 relates to a barbituric acid radioimmunoassay while U.S. Pat. No. 3,704,282 discloses a catecholamine radioimmunoassay. Numerous other radioimmunoassays are described in the patent and scientific literature. However, in all instances such assays were developed and utilized in individual manner for single type testing. No method has been heretofore disclosed for combining two or more assays into a single test procedure.

DESCRIPTION OF THE INVENTION

The present invention relates to compositions useful for conducting a plurality of different radioimmunoassays simultaneously, as well as to methods which can be employed to prepare such compositions. By utilizing the compositions of the present invention one is able to conduct screening tests for several desired substances simultaneously in a highly efficient manner. Since in most screening situations the large majority of samples produce negatives, only a relatively few samples will provide a positive radioactive count level. While it is not possible to determine directly from a positive result which of the substances being tested for are in fact present, this can be determined by running the original sample through the individual assays. However, the overall savings in time and effort are readily apparent from the tremendously reduced number of test runs required by the present procedure when compared to conducting a screen for the same substances using the individual assay procedures on all the original samples.

The compositions of the present invention comprise a plurality of labeled antigens and their respective antibodies, all the aforesaid being present in selected concentrations so that the response curves observed for each antigen are essentially superimposable on the response curve of all other antigens present in the composition.

The simultaneous multiple radioimmunoassay is based on the fundamental principles of single radioimmunoassays. Radiolabeled antigens and unlabeled antigens are competitively bound to their respective antibodies in proportion to their concentration in the solution. Each unlabeled antigen displaces its radioactive antigen from the limited specific antibody present. By careful manipulation of the concentrations of the respective antigens and antibodies, the standard curves for the substances to be detected can be closely superimposed As a consequence, a very similar response is obtained from a specimen containing one or more of the subject substances.

Superimposing of the response curves of the radiolabeled antigens can be readily accomplished by utilizing the following procedure:

First, one of the labeled antigens is provided for the composition in a concentration to give a desired range of counts. Then a response curve is prepared using a number of different concentration levels for the antibody specific to the said labeled antigen. It is then possible to select the concentration level of antibody which yields a response curve corresponding to a sensitivity range desired for the assay.

Thereafter, a second labeled antigen is provided at a concentration yielding any arbitrary count level. Response curves are then obtained using varying concentrations of antibody specific to the aforesaid second labeled antigen. The antibody concentration which yields an assay sensitivity and a response curve shape which approximates the assay sensitivity and response curve exhibited for the first antigen and antibody is then selected. Finally, the amplitude of the second response curve is adjusted up or down by making an appropriate adjustment in the concentration of the second labeled antigen. This procedure may then be repeated for each of the other antigen-antibody combinations which are to be included in the simultaneous multiple radioimmunoassay composition.

In preparing the aforesaid standard curves it is not necessary that the concentration ranges for each antigen be identical but can be in a ratio that can vary by several powers of magnitude.

Suitable test substances for which simultaneous multiple radioimmunoassay compositions can be prepared include the following:

opium alkaloids, such as morphine, heroin, codeine, etc. barbiturates, such as secobarbital, butabarbital, phenobarbital, etc., amphetamines, such as amphetamine and metamphetamine, catecholamines, such as norepinephrine, dopamine, epinephrine, etc., peptides such as angiotensin, bradykinin, insulin, etc. proteins, such as CEA, placentalactogen, placental alkaline phosphatase, alpha-fetoprotein, etc., steroids such as estriol, estradiol, estrone, testosterone, etc., viral antigens, such as influenza, polio, hepatitis, etc., bacterial antigens such as Neisseria gonorrheae, Treponema pallidum, protozoa, etc. antibodies such as those found in Lupus erythematosus, rheumatoid arthritis, etc., and any other materials which can be utilized as immunological screening tests.

The term "labeled antigen" is meant to include antigen molecules which are labeled with a radioactive element, such as for example, tritium, iodine-125, carbon-14, or any other suitable radioactive element employed in radioassay. A particularly preferred radioactive element is iodine-125 which may be incorporated by methods known per se into morphine or secobarbital and amphetamine derivatives. Labeled antigens for use in the practice of the present invention are now generally articles of commerce and thus are readily available.

In order to introduce the $^{125}$I label it may be necessary that the antigen molecule be derivatized preferably with a pendant phenolic group which may be linked to the antigen by a $C_1$-$C_5$ alkylene linking group. Suitable derivatives for this purpose include rac. 4-hydroxy-alpha-methylphenethylamine useful as an amphetamine derivative and 5-allyl-5-[1-(p-hydroxyphenethyl-carbamyl)-2-propyl] barbituric acid useful as a secobarbital derivative.

EXAMPLE 1

The preparation of a dual assay system incorporating radioimmunoassays for morphine and barbituates is described herein.

Materials and Methods a. Test Reagent Formulation (for 100 tests)

1. Two ml. $^{125}$I derivative of morphine diluted in phosphate buffered saline (PBS) to give between 30,000 and 35,000 CPM per 20μ 1) and 2 ml. $^{125}$I derivative of secobarbital (diluted in PBS to give between 40,000 and 45,000 CPM per 20 μl) are mixed. To this solution 16 ml. of PBS are added. For most antisera the above concentrations of labeled antigens were found to be satisfactory. At times it became necessary to change the ratio of the morphine to barbital concentrations to achieve proper matching of the standard curves.

2. The morphine and barbiturate antisera are diluted to 2× the strength used in the single assays. Each antiserum is then mixed with equal amounts of PBS. To the flask containing the labels 10 ml. of the morphine and barbiturate antisera solutions are added. The premix is incubated at 4°C. overnight.

b. Testing Procedure

1. Add 0.4 ml. of the premix reagent to each of a series of 10 × 75 mm glass tubes.

2. Add 0.1 ml. of each of the normal human urine, 50 ng/ml., 100 ng/ml., 200 ng/ml., and 500 ng/ml. standards for each of the two drugs to the glass tubes. Run each standard in duplicate. Proceed with the testing as if it was a single drug assay.

c. Evaluation of Each Standard Curve

Using linear graph paper record the counts per minute (CPM) on the vertical axis and on the horizontal x-axis the nanograms per ml. of drug. Plot the average value in CPM of the two tubes containing the 0 ng/ml., 50 ng/ml., 100 ng/ml., 200 ng/ml. and 500 ng/ml. standards of both morphine and barbital. Fit the best lines through the two sets of points.

Each curve separately must meet the desired sensitivity requirement for the test in question. If the curves do not fulfill these requirements it is necessary to proceed as though it was a single antigen until both curves do.

d. Matching

1. Average the CPM for the 100 ng/ml. standards of morphine and barbital. This number will be referred to as the "Combined 100 ng/ml. control average" (CCA).

2. Subtract the CPM of the 100 ng/ml. morphine standard from the CCA. This difference should be less than 3.5% of the CCA value.

3. Follow the same procedure at the 200 ng/ml. and 500 ng/ml. level.

If all the requirements described above are fulfilled the curves are considered satisfactorily matched. If not, the following steps will be necessary:

4. Select the curve with the highest difference in counts between 50 ng/ml. and 100 ng/ml., 100 ng/ml. and 200 ng/ml. and finally 200 ng/ml. and 500 ng/ml. The antibody dilution for the selected curve is left unchanged throughout the rest of the matching process.

5. If the CPM for the 100 ng/ml, 200 ng/ml. and 500 ng/ml. for the selected curve are larger than for the other drug, then three premixes must be made using decreasing antibody concentrations for the second drug. On the other hand, if the CPM for the 100 ng/ml, 200 ng/ml. and 500 ng/ml. for the best curve are smaller than for the other drug, then three premixes must be made using increasing antibody concentrations for the second drug.

6. The curves obtained with each one of the premixes are analyzed according to the requirements for "matched curved". The best combination is selected. If still not all the requirements are fulfilled, further antibody dilutions for the second drug must be tried in order to bring the two curves as close as possible, leaving the antibody dilution for the selected curve constant. Follow the same line of reasoning described in section 5 above for the first attempt at matching.

Results

The morphine-barbiturate dual assay has been evaluated using urine from "normal" individuals from a random population, volunteers administered morphine intravenously and volunteers administered oral doses of barbiturates. All specimens were screened employing Abuscreen Radioimmunoassay for Morphine ($^{125}$I), Abuscreen Radioimmunoassay for Barbiturates and the morphine-barbiturate dual assay, in order to compare the results obtained with a single versus the dual assay system.

Table I gives a summary of the results from 117 "normal" urines. Of these urines, 114 were found to be negative by all three assays and 3 were found to be negative by the morphine assay and positive by the barbiturate and dual assays.

TABLE I

Comparison of Results Obtained with "Normal" Human Urines Using Single and Dual Assay Systems

| Number of Individuals | Single Assay[a] Systems Morphine | | Dual Assay[b] Systems Barbiturate |
|---|---|---|---|
| 114 | − | − | − |
| 3 | − | + | + |

[a]A sample was considered positive if it contained over 100 ng of morphine or secobarbital equivalents/ml.
[b]A sample was considered positive when the counts per minute (cpm) were equal to or greater than the cpm of the positive controls.

The results obtained with urines from individuals receiving morphine or barbiturates are presented in Tables II and III. Excellent correlation between the single and dual assays was observed in all the specimens tested.

TABLE II

Comparison of the Single and the Dual Assay Results in Detecting Morphine in Urine of 12 Individuals Receiving Morphine Intravenously[a]

| Patient No. | Time (hrs.) | Single Assay Morphine (ng ME[b]/ml) | Barbiturate (ng SE[c]/ml) | Dual Assay[d] |
|---|---|---|---|---|
| 1 | 0 | 0 | 4 | − |
|  | 0–8 | 7979 | 0 | + |
|  | 8–16 | 1433 | 0 | + |
|  | 16–24 | 732 | 0 | + |
|  | 24–36 | 914 | 0 | + |
|  | 36–48 | 626 | 0 | + |
|  | 48–60 | 106 | 5 | + |
|  | 60–72 | 80 | 7 | − |
| 2 | 0 | 0 | 5 | − |
|  | 0–8 | 2000 | 7 | + |
|  | 8–16 | 393 | 0 | + |
|  | 16–24 | 266 | 3 | + |
|  | 24–36 | 587 | 6 | + |
|  | 36–48 | 192 | 5 | + |
|  | 48–60 | 91 | 4 | + |
|  | 60–72 | 21 | 0 | − |

[a]Results presented are representative examples from a total of 12 volunteers. All volunteers received a 10 mg. dose per 70 kg., i.v.
[b]Morphine equivalents by the $^{125}$I assay.
[c]Secobarbital equivalents by the $^{125}$I assay.
[d]A sample was considered positive when the counts per minute (cpm) were equal to or greater than the cpm of the positive controls.

TABLE III

Comparison of the Single and Dual Assay Results in Detecting Barbiturates in Urine from 13 Individuals Receiving Standard Doses of Barbiturates[a]

| Patient No. | Time (hrs.) | Single Assay Morphine (ng ME[b]/ml.) | Barbiturate (ng SE[c]/ml.) | Dual Assay[d] |
|---|---|---|---|---|
| 1 | 0 | 0 | 0 | − |
|  | 1–4 | 0 | >500 | + |
|  | 4–8 | 0 | >500 | + |
|  | 8–12 | 0 | >500 | + |
|  | 12–24 | 0 | >500 | + |
|  | 24–48 | 0 | >500 | + |
|  | 48–72 | 0 | >500 | + |
| 2 | 0 | 0 | 10 | − |
|  | 1–4 | 0 | 170 | + |
|  | 4–8 | 2 | 200 | + |
|  | 8–12 | 0 | 300 | + |
|  | 12–24 | 0 | 350 | + |
|  | 24–48 | 0 | >500 | + |
|  | 48–72 | 0 | 260 | + |

[a]Results presented are representative examples from a total of 13 volunteers. Patient No. 1 received a 100 mg. oral dose of secobarbital and patient No. 2 received a 100 mg. oral dose of butabarbital.
[b]Morphine equivalents by the I$^{125}$ assay.
[c]Secobarbital equivalents by the I$^{125}$ assay.
[d]A sample was considered positive when the counts per minute (cpm) were equal to or greater than the cpm of the positive controls.

EXAMPLE 2

The preparation of a triple assay system, incorporating radioimmunoassays for morphine, barbiturates and amphetamines is described herein.

By careful manipulation of the concentrations of morphine, secobarbital and amphetamine, radiolabeled antigens and antibodies, the standard curves for the three drugs can be closely superimposed.

MATERIALS AND METHODS a. Test Reagent Formulation (for 100 tests)

1. Three ml. $^{125}$I derivative of morphine (diluted in PBS to give between 30,000 and 35,000 CPM per 20μ 1), 3 ml. $^{125}$I derivative of secobarbital (diluted in PBS to give between 40,000 and 45,000 CPM per 20μ 1) and 3 ml. $^{125}$I derivative of amphetamine (diluted in PBS to give between 30,000 and 35,000 CPM per 20μ 1) are mixed. To this solution 21 ml. of PBS are added. For most antisera the above concentrations of labeled antigens were found to be satisfactory.

2. The morphine, barbiturate and amphetamine antisera are diluted to 3x the strength used in the single assays. Each antiserum is then mixed with equal amounts of PBS. To the flask containing the labels 10 ml. of the morphine, barbiturate and amphetamine antisera solutions are added. The premix is incubated at 4°C. overnight.

b. Testing Procedure

Same as for the dual assay in Example 1 except that standards for each of the three drugs must be used. The amphetamine standards are 500 ng/ml., 1000 ng/ml., 2000 ng/ml and 5000 ng/ml.

c. Evaluation of Each Standard Curve

Same as for the dual assay in Example 1.

Matching

The matching is done identical to the procedure of Example 1. First, the morphine and barbital curves are matched. Subsequently, the amphetamine curve is manipulated until it is essentially superimposed on the response curve of the other two drugs. In the case of amphetamine, all concentrations are 10x those of morphine and barbital, i.e., the 100 ng/ml. morphine or barbital standards would give a similar response to 1000 ng/ml. amphetamine; the 200 ng/ml. morphine or barbital standards would correspond to 2000 ng/ml. amphetamine, etc.

Results

The triple assay system has been evaluated using urine from "normal" individuals from a random population, volunteers administered morphine intravenously and volunteers administered oral doses of barbiturates. All specimens were screened employing Abuscreen Radioimmunoassay for Morphine ($^{125}$I), Abuscreen Radioimmunoassay for Barbiturates, Abuscreen Radioimmunoassay for Amphetamine ($^{125}$I) and the triple assay system, in order to compare the results obtained with a single versus a triple assay system.

Table IV gives a summary of the results from 117 "normal" urines. Of these urines, III were found to be negative by all four assays, 3 were found to be negative by the morphine and amphetamine assays and positive by the barbiturate and triple assays. Finally, 3 were found to be negative by the morphine and barbiturate assays and positive by the amphetamine and triple assays.

TABLE IV

Comparison of Results Obtained in "Normal" Human Urines Using Single and Triple Assay Systems

| No. of Individuals | Single Assay[a] Systems Morphine | Barbiturate | Amphetamine | Triple Assay[b] Systems |
|---|---|---|---|---|
| 111 | − | − | − | − |
| 3 | − | + | − | + |
| 3 | − | − | + | + |

[a]A sample was considered positive if it contained over 100 ng of morphine or secobarbital equivalents/ml. or over 1000 ng of amphetamine equivalents/ml.
[b]A sample was considered positive when the counts per minute (cpm) were equal to or greater than the cpm of the positive controls.

The results obtained with urines from individuals receiving morphine and barbiturates are presented in Tables V and VI. Excellent correlation between the single and triple assays was observed in all the specimens tested.

TABLE V

Comparison of the Single and the Triple Assays in Detecting Morphine in Urine of 12 Individuals Receiving Morphine Intravenously[a]

| Patient No. | Time (hrs.) | Morphine (ng ME[b]/ml) | Single Assays Barbiturate (ng SE[c]/ml) | Amphetamine (ng AM[d]/ml) | Triple Assay[e] |
|---|---|---|---|---|---|
| 1 | 0 | 0 | 4 | 0 | — |
|   | 0–8 | 7979 | 0 | 0 | + |
|   | 8–16 | 1433 | 0 | 0 | + |
|   | 16–24 | 732 | 0 | 0 | + |
|   | 24–36 | 914 | 0 | 100 | + |
|   | 36–48 | 626 | 0 | <50 | + |
|   | 48–60 | 106 | 5 | 0 | + |
|   | 60–72 | 80 | 7 | 150 | + |
| 2 | 0 | 0 | 5 | 0 | — |
|   | 0–8 | 2000 | 7 | 0 | + |
|   | 8–16 | 393 | 0 | 150 | + |
|   | 16–24 | 266 | 3 | 0 | + |
|   | 24–36 | 587 | 6 | 50 | + |
|   | 36–48 | 192 | 5 | 0 | + |
|   | 48–60 | 91 | 4 | 0 | + |
|   | 60–72 | 21 | 0 | 0 | — |

[a]Results presented are representative examples of a total of 12 volunteers. All volunteers received a 10 mg. dose per 70 kg., i.v.
[b]Morphine equivalents by the $^{125}$I assay.
[c]Secobarbital equivalents by the $^{125}$I assay.
[d]Amphetamine equivalents by the $^{125}$I assay.
[e]A sample was considered positive when the counts per minute (cpm) were equal to or greater than the cpm of the positive controls.

TABLE VI

Comparison of the Single and Triple Assays in Detecting Barbiturates in Urine from Thirteen Individuals Receiving Standard Doses of Barbiturates[a]

| Patient No. | Time (hrs.) | Morphine (ng ME[b]/ml) | Single Assay Barbiturate (ng SE[c]/ml) | Amphetamine (ng AM[d]/ml) | Triple Assay[e] |
|---|---|---|---|---|---|
| 1 | 0 | 0 | 0 | 0 | — |
|   | 0–1 | 0 | 7500 | 50 | + |
|   | 1–4 | 0 | 7500 | 25 | + |
|   | 4–8 | 0 | 7500 | 75 | + |
|   | 8–12 | 0 | 7500 | 25 | + |
|   | 12–24 | 0 | 7500 | 0 | + |
|   | 24–48 | 0 | 7500 | 50 | + |
|   | 48–72 | 0 | 7500 | 75 | + |
| 2 | 0 | 0 | 10 | 350 | — |
|   | 0–1 | 0 | 170 | 700 | + |
|   | 1–4 | 0 | 200 | 50 | + |
|   | 4–8 | 2 | 300 | 150 | + |
|   | 8–12 | 0 | 350 | 300 | + |
|   | 12–24 | 0 | 310 | 200 | + |
|   | 24–48 | 0 | 7500 | 400 | + |
|   | 48–72 | 0 | 260 | 200 | + |

[a]Results presented are representative examples of a total of 13 volunteers. Patient No. 1 received a 100 mg. oral dose of secobarbital and Patient No. 2 received a 100 mg. dose of butabarbital.
[b]Morphine equivalents by the $^{125}$I assay.
[c]Secobarbital equivalents by the $^{125}$I assay.
[d]Amphetamine equivalents by the $^{125}$I assay.
[e]A sample was considered positive when the counts per minute (cpm) were equal to or greater than the cpm of the positive controls.

EXAMPLE 3

The preparation of materials used in the amphetamine radioimmunoassay is described in this example.

t-Butyl ester of rac. N-(4-hydroxy-alpha-methylphenethyl)carbamic acid

In a 1 liter, three neck. r.b. flask equipped with a stirrer, thermometer, and gas inlet tube for nitrogen were placed 46.42 g. of rac. 4-hydroxy-alphamethylphenethyl amine hydrobromide (0.2 mole), 300 ml. of water, 300 ml. of dioxane and 12 g. of magnesium oxide (0.3 mole). The mixture was stirred at 40°–45° for 18 hours. The cooled, pale amber, turbid solution was brought from pH 8 to pH 5 by addition of a few ml. of acetic acid and the dioxane distilled in a rotary evaporator. To the resulting mixture of two liquid phases, 500 ml. of water was added and the organic phase collected by five 100 ml. extractions with n-butanol. The combined extracts were washed with two small portions of water, then dried over MgSO$_4$. After removal of the drying agent, the solvent was distilled in a rotary evaporator. The last traces of n-butanol were removed by the addition of 150 ml. of toluene and distillation in the rotary evaporator, finally at a pot temperature of 75°. The residue, 51 g., crystallized under petroleum ether, m.p. 93°–95.5°. This was dissolved in 350 ml. of 60°–90° petroleum ether and 150 ml. of ethyl acetate, treated with a little Alox, filtered, and to the warm filtrate, 450 ml. of 60°–90° petroleum ether was added. After cooling to room temperature the mixture was chilled in an ice bath for 4 hours, the crystalline product collected by filtration, washed with a little 60°–90° petroleum ether and dried. Yield 32.6 g.

(65%), m.p. 98.5°–101.5°.

Microanalysis: C, 67.14; H, 8.54; N, 5.55 Calc. for $C_{14}H_{21}NO_3$ (251.32): C, 66.91; H, 8.42; N, 5.57

The mother liquor was stripped of solvent and covered with 100 ml. of 60°–90° petroleum ether plus a few ml. of ethyl acetate. After chilling for several hours, another 3 g. of product, m.p. 97.5°–100°, was obtained; this was also used in the next stage.

Ethyl ester of rac. 4-(2-t-butoxycarbonamidopropyl)phenoxyacetic acid

Thirty-two g. of the above described rac. N-(4-hydroxy-alpha-methylphenethyl)carbamic acid t-butyl ester (0.127 mole) was dissolved in 350 ml. of hexamethylphosphoric triamide in a 1 liter, r.b.-flask provided with a stirrer, thermometer and inlet tube for nitrogen. To this solution, cooled to 0°–2°, was added the sodium hydride obtained by washing 6.1 g. of the 57% dispersion in mineral oil (0.144 mole) three times with pentane. After 2 hours, hydrogen evolution became very slow, and a thick paste of the sodium salt resulted. To this suspension, 21.5 g. of ethyl bromoacetate (0.128 mole) in 25 ml. of benzene was added at once; the mixture began to thin out immediately with only a slight rise in temperature (2°). The mixture was stirred for 2 hours at 0°–2°, then allowed to stand at room temperature for 12 hours. To the clear amber solution, 750 ml. of ice and water was added, and the oil that separated was collected by five extractions with 125 ml. portions of ether. The combined extracts were freed of traces of the triamide by several small washes with water. After drying over $MgSO_4$ and distillation of the solvent, there remained 43 g. of pale amber oil. One g. of this oil was distilled in a "Bantam-Ware" short path still and but for a small forerun (solvent) the entire pot content distilled as a very pale colored viscous oil at 163°–166°/0.03 mm.

Microanalysis: C, 64.14; H, 8.13; N, 4.40 Calc. for $C_{18}H_{27}NO_5$ (337.43): C, 64.08; H, 8.07; N, 4.15 rac. 4-(2-t-butoxycarbonamidopropyl)phenoxyacetic acid

Forty-one g. of the above undistilled ester, ethyl ester of rac. 4-(2-t-butoxycarbonamidopropyl)phenoxyacetic acid, was heated on the steam bath with 100 ml. of water and to the stirred solution, 10% sodium hydroxide was added until a permanent pH of 9 was obtained. At this point the hydrolysate remained at room temperature overnight. After four extractions with 50 ml. portions of chloroform to remove neutral material, the solution was cooled to 10°, and brought to pH 3 by the addition of 25% citric acid. An oil separated that soon solidified. The oil was dissolved by the addition of 1800 ml. of chloroform, the aqueous layer separated, and the chloroform solution washed twice with small portions of water and dried. After removal of the drying agent and distillation of the solvent, there remained 35.5 g. of a white solid, m.p. 137°–139° dec. This solid was dissolved in 1 l. of hot toluene and allowed to crystallize overnight at room temperature. The product, after drying, first at 65° in vacuo, and then 100°, weighed 29.1 g., m.p. 144.5°–146.5°.

N-hydroxysuccinimide ester of rac. 4-(2-t-butoxycarbonamidopropyl)phenoxyacetic acid To a chilled solution of 15.47 g. (0.05 mole) or rac. 4-(2-t-butoxycarbonamidopropyl)phenoxyacetic acid and 6.5 g. (0.057 mole) of N-hydroxysuccinimide in 250 ml. of ethylene glycol dimethyl ether was added a solution of 11.33 g. (0.055 mole) of dicyclohexylcarbodiimide in 100 ml. of ethylene glycol dimethyl ether. Within a few minutes the solution began to deposit dicyclohexylurea. This mixture was refrigerated for 60 hours at 4°, then the dicyclohexylurea was removed by filtration and the solvent distilled from the filtrate in a rotary evaporator. The residue weighed 21.1 g., m.p. 143.5°–145.5° and recrystallized from 350 ml. of 2-propanol. After chilling in an ice bath for 6 hours, 18 g. of crystalline solid was recovered, m.p. 149°–151.5°.

Microanalysis: C, 59.07; H, 6.64; N, 6.79 Calc. for $C_{20}H_{26}N_2O_7$ (406.44): C, 59.10; H, 6.45; N, 6.89

Preparation of Immunogen (Bovine Serum Albumin Conjugate of 4-(2-aminopropyl)phenoxyacetic acid Bovine serum albumin (300 mg.) was dissolved in 12 ml. of water and 6 ml. of 0.5 M sodium bicarbonate was added. The N-hydroxysuccinimide ester (61 mg.) was dissolved in 6 ml. of dimethoxyethane and added dropwise to the BSA solution with stirring. The solution was stirred for 4 hours at room temperature, then allowed to stand 4° overnight. The solution was then diluted to approximately 50 ml. with water and concentrated by ultrafiltration (Amicon PM-10 membrane) to 5–10 ml. This dilution and concentration procedure was carried out at least four times, or until the $A_{260}$ of the filtrate had decreased from approximately 25 to less than 0.2. The final concentrate was dialyzed overnight at 4° against 1 liter of water. The dialysate was changed and dialysis repeated twice for about 4 hours each time. The solution was then lyophilized. The lyophilized material was redissolved in 10 ml. of trifluoroacetic acid/dichloromethane (1:1, v/v) and allowed to stand for at least 30 minutes in the dark at room temperature. The purple solution was then evaporated to dryness under a stream of nitrogen. The purple residue was resuspended in 20 ml. of water and brought to pH 6–9 with 1 N sodium hydroxide. The resulting clear, colorless solution was dialyzed against one liter of phosphate buffered saline (0.9% NaCl in 0.005 M sodium phosphate, pH 7.2) overnight at 4°. The dialysate was changed and dialysis continued for 4 hours.

The degree of incorporation of hapten in two immunogen preparations was estimated at 30–50 moles of hapten per mole of BSA by radioimmunoassay. The molecular weight of the immunogen from one preparation was estimated by electrophoresis on a gradient polyacrylamide gel slab in the presence of sodium dodecyl sulfate. The average electrophoretic mobility of the immunogen was slightly less than that of BSA and corresponded to a molecular weight of about 72,000, indicating incorporation of approximately 20 moles of hapten per mole of BSA, in reasonable agreement with the results of radioimmunoassay.

Immunization and Bleeding

For immunization of goats, the dialyzed material was diluted with phosphate buffered saline to an $A_{274}$ of approximately 1.0. The diluted immunogen was then emulsified with an equal volume of Freund's adjuvant. The first three inoculations (using complete adjuvant) were administered at weekly intervals, the fourth after another three weeks, and monthly thereafter (the fourth and successive inoculations used incomplete adjuvant). Each inoculation comprised two subcutaneous injections of 0.5 ml. each.

Test bleedings were taken two, three and four weeks after the first inoculation. After five weeks, and at biweekly intervals thereafter, 300 ml. of blood was drawn and serum prepared by standard techniques.

Preparation of Labeled rac. 4-hydroxy-alpha-methylphenethylamine hydrobromide

The radioactive amphetamine analog was prepared by iodination with $^{125}$I using techniques known per se. The substrate for iodination was rac. 4-hydroxyalpha-methylphenethylamine hydrobromide (2 mg/ml. in 0.05 M sodium borate, pH 8.5).

The foregoing disclosure regarding the amphetamine assay taken as an independent test is not to be considered as part of the present invention, but is being presented herein for the purpose of insuring a complete disclosure in support of the polyvalent assay hereinbefore described.

While the assay of the instant invention has been discussed above with special reference to radioimmunoassay procedures, it should be noted that alternate methods of labeling antigens are known in the art as are corresponding assay techniques to employ them. Thus, other labeled antigens which may be employed in multiple assays of the present invention include fluorescent-labeled antigens, free-radical labeled antigens, enzyme-labeled antigens and the like. It is within the skill of the art to employ such labeled antigens in the practice of the instant invention.

EXAMPLE 4

N-[2-(4-hydroxyphenyl)ethyl]-2-[4-(2-aminopropyl)-phenoxy] acetamide (a) Into a 100 ml. flask equipped for stirring, with thermometer, and under nitrogen were placed 1.8 g. (5.8 × 10$^{-3}$ mole) of DL-3-[2-(t-butoxycarbamido)-propyl]phenoxyacetic acid, 45 ml. of dry tetrahydrofuran and 1.0 g (6.05 × 10$^{-3}$ mole) of carbonyl diimidazole. The mixture was stirred at room temperature (21°C.) for 2 hours when 0.63 g. (4.6 × 10$^{-3}$ mole) of tyramine was added. Stirring was continued at 21°C. overnight (ca. 18 hours). The mixture was then transferred to a separatory funnel and diluted with several volumes of ethyl acetate. The mixture was shaken with 3 portions of water. The organic phase was separated, dried over anhydrous sodium sulfate and evaporated at reduced pressure to give 2.6 g. of N-[2-(4-hydroxyphenyl)ethyl]-2-[4-t-butoxycarbonamidopropyl)-phenoxy]acetamide, identified by nuclear magnetic resonance spectroscopy.

(b) Into a 100 ml. flask equipped with thermometer, stirrer, and under nitrogen, were placed 1.97 g. of the product of step (a) and 28.4 ml. of trifluoroacetic acid. After stirring for 1 hour at room temperature (21°C.), the mixture was concentrated at 40°C. The residue was dissolved in 15 ml. of water and placed on a 15 mm × 150 mm column of ion exchange resin (IR-4B, acetate form) and eluted with water. Approximately ten 15 ml. fractions were collected, containing only the desired material. Evaporation of the combined fractions left a residue of 2.5 g. which was dissolved in water, neutralized by addition of solid sodium bicarbonate and stored in the refrigerator until precipitation was complete. After washing with cold water and crystallization, 0.4 g., m.p. 160-163°C. was obtained. By further cooling, and concentrations, additional product was obtained to total 0.52 g. of N-[2-(4-hydroxyphenyl)ethyl]-2-[4-(2-aminopropyl)-phenoxy]acetamide.

Anal. Calcd. for $C_{19}H_{24}N_2O_3$; C, 69.49; H, 7.37; N, 8.53. Found: C, 69.41; H, 7.46; N, 8.40. NMR spectrum: Compatible

We claim:

1. A composition useful as a reagent for carrying out multiple radioimmunoassays simultaneously for a plurality of desired test substances wherein a positive result in such assays indicates the presence of one or more of the desired test substances which composition comprises (i) a plurality of labeled antigens corresponding to the test substances to be detected, and (ii) antibodies directed to each of said antigens, wherein said labeled antigens and their respective antibodies are present in concentrations selected to produce a response curve for each antigen which is substantially superimposable upon the response curves of all the other antigens present in said composition.

2. The composition of claim 1 wherein two labeled antigens and their respective antibodies are present.

3. The composition of claim 2 wherein said two labeled antigens are radiolabeled morphine and a radiolabeled 5- or 5,5-substituted barbituric acid derivative.

4. The composition of claim 3 wherein said two labeled antigens are morphine ($^{125}$I) and a secobarbital ($^{125}$I) derivative.

5. The composition of claim 1 wherein three labeled antigens and their respective antibodies are present.

6. The composition of claim 5 wherein said three labeled antigens are radiolabeled morphine, a radiolabeled amphetamine derivative and a radiolabeled 5- or 5,5-substituted barbituric acid derivative.

7. The composition of claim 6 wherein said three labeled antigens are morphine ($^{125}$I), an amphetamine ($^{125}$I) derivative and a secobarbital ($^{125}$I) derivative.

8. A method for preparing compositions useful as reagents for carrying out multiple radioimmunoassays simultaneously for a plurality of desired test substances wherein a positive result in such assays indicates the presence of one or more of said desired test substances which method comprises:

A. providing a first radiolabeled antigen corresponding to one of the test substances to be detected in a concentration selected to yield a desired range of counts;

B. preparing response curves for said first antigen utilizing a number of different concentration levels of an antibody specific to said first antigen and selecting one of said concentration levels which provdes a desired sensitivity range;

C. providing a second radiolabeled antigen corresponding to a second of the test substances to be detected at an arbitrary concentration level;

D. preparing response curves for said second antigen utilizing a number of different concentration levels of an antibody directed to said second antigen and selecting a concentration level which provides a response curve having a shape and a sensitivity range as close as possible to the response curve selected for said first antigen.

E. adjusting the concentration level of said second antigen so as to raise or lower the amplitude of the selected response curve from said second antigen so as to essentially superimpose that response curve with the selected response curve of said first antigen; and F. repeating steps D and E with any other antigens needed to detect the desired test substances.

9. The method of claim 8 wherein two test substances are to be detected and said composition to be prepared comprises two corresponding antigens and antibodies selective thereto.

10. The method of claim 9 wherein three test substances are to be detected and said composition to be prepared comprises three corresponding antigens and antibodies selective thereto.

11. A method for the simultaneous assay of a plurality of test substances in a sample which method comprises:

mixing said sample with a known amount of a plurality of (i) labeled antigens correspondng to said test substances to be detected and (ii) antibodies directed to each of said antigens, wherein said labeled antigens and their respective antibodies are present in concentrations selected to produce a response curve for each antigen which is substantially superimposable upon the response curves of all the other antigens present in said composition;

detecting the presence of any unbound lebeled antigen after the mixture has equilibrated;

comparing the level of unbound labeled antigen observed with levels obtained by utilizing positive controls in said assay, the sample being considered positive to the presence of one or more test substances if said level of unbound labeled antigen is equal or greater than the level observed with said controls.

12. The method of claim 11 wherein said assay method is radioimmunoassay.

13. The method of claim 12 wherein the test substances to be detected are opium alkaloids and barbiturates, the antigens employed are a radiolabeled morphine and a radiolabeled 5- or 5,5-substituted barbituric acid derivative and the antibodies employed are those specific respectively to the aforesaid antigens.

14. The method of claim 13 wherein said radiolabeled antigens are morphine ($^{125}$I) and a secobarbital ($^{125}$I) derivative.

15. The method of claim 12 wherein the test substances to be detected are opium alkaloids, barbiturates and amphetamines, the antigens employed are a radiolabeled morphine, a radiolabeled 5- or 5,5-substituted barbituric acid derivative and a radiolabeled amphetamine derivative and the antibodies employed are those directed respectively to the aforesaid antigens.

16. The method of claim 15 wherein said radiolabeled antigens are morphine ($^{125}$I), a secobarbital ($^{125}$I) derivative and an amphetamine ($^{125}$I) derivative.

* * * * *